United States Patent
Lee et al.

(10) Patent No.: US 11,360,105 B2
(45) Date of Patent: Jun. 14, 2022

(54) METHOD OF EVALUATING ADRENAL STEROIDS IN SALIVA COLLECTED BY COTTON SWAB

(71) Applicant: KOREA INSTITUTE OF SCIENCE AND TECHNOLOGY, Seoul (KR)

(72) Inventors: Chae Lin Lee, Seoul (KR); Jung Hee Kim, Seoul (KR); Man Ho Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 651 days.

(21) Appl. No.: 16/395,069

(22) Filed: Apr. 25, 2019

(65) Prior Publication Data
US 2020/0141952 A1    May 7, 2020

(30) Foreign Application Priority Data

Nov. 7, 2018    (KR) ........................ 10-2018-0135752

(51) Int. Cl.
G01N 33/48 (2006.01)
G01N 33/74 (2006.01)

(52) U.S. Cl.
CPC .................................. *G01N 33/743* (2013.01)

(58) Field of Classification Search
None
See application file for complete search history.

(56) References Cited

U.S. PATENT DOCUMENTS

2016/0231341 A1    8/2016    Lakshmi Narayanan et al.

FOREIGN PATENT DOCUMENTS

| KR | 10-1029251 B1 | 4/2011 |
| KR | 10-2012-0076051 A | 7/2012 |
| KR | 10-1228322 B1 | 1/2013 |
| KR | 10-2016-0053979 A | 5/2016 |

OTHER PUBLICATIONS

Pizzato et al (Toxicology Mechanisms and Methods, 2017, vol. 27, No., pp. 641-656). (Year: 2017).*
Sanchez et al (Journal of Chromatography A, 2012, vol. 1248, pp. 178-181). (Year: 2012).*
Salivette user instruction.*
Communication from Korean Intellectual Property Office for Non-Final Office Action dated Jan. 7, 2020 of the Korean patent application No. 10-2018-0135752, which corresponds to the present application.
Tomoaki Kozaki et al. Effects of saliva collection using cotton swab on cortisol enzyme immunoassay, Eur J Appl Physiol, Aug. 29, 2009, pp. 743-746, vol. 107.
Ilias Perogamvros et al. Simultaneous measurement of cortisol and cortisone in human saliva using liquid chromatography—tandem mass spectrometry: Application in basal and stimulated conditions, Journal of Chromatography B, Sep. 18, 2009, pp. 3771-3775, vol. 877.
Giorgia Antonelli et al. Salivary cortisol and cortisone by LC—MS/MS: validation, reference intervals and diagnostic accuracy in Cushing's syndrome, Clinica Chimica Acta, Oct. 9, 2015, pp. 247-251, vol. 451.

* cited by examiner

*Primary Examiner* — Celine X Qian
(74) *Attorney, Agent, or Firm* — Goldilocks Zone IP Law

(57) ABSTRACT

The present invention relates to a method for evaluating metabolic activity based on the concentrations of cortisol and its precursors and metabolites thereof in saliva collected by a swab for the measurement of adrenal steroids relating to biochemical stress evaluation and more particularly, to a method of comparing metabolic activity of physiologically different adrenal steroids by analyzing adrenal steroids including cortisol and cortisone extracted from a trace amount of saliva by mass spectrometry and evaluating the metabolic ratio between the two compounds as well as the absolute amount of each compound. Accordingly, the present invention can be utilized as an index for evaluating response to biochemical stress and related diseases by measuring the amounts of adrenal steroids including cortisol and cortisone in a trace amount of saliva collected with a swab.

10 Claims, 2 Drawing Sheets

FIG. 2
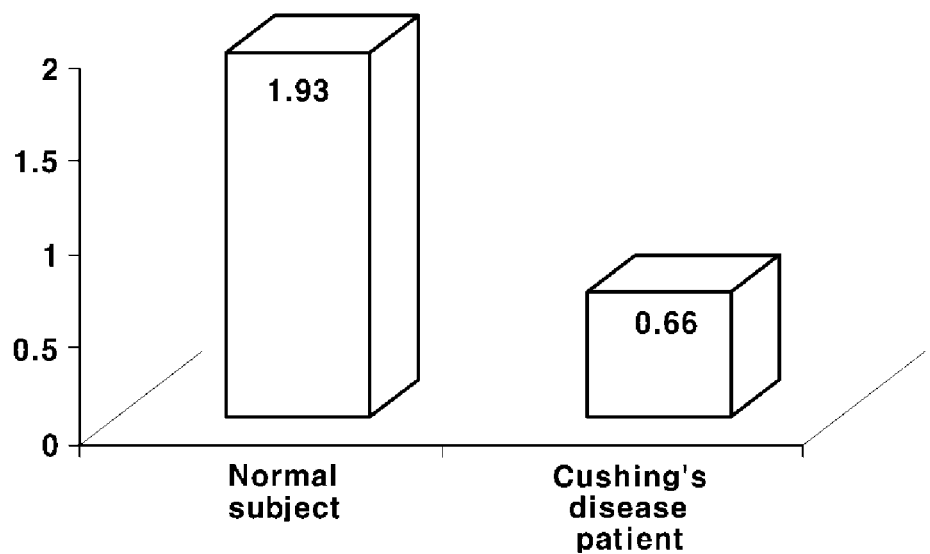
FIG. 2a
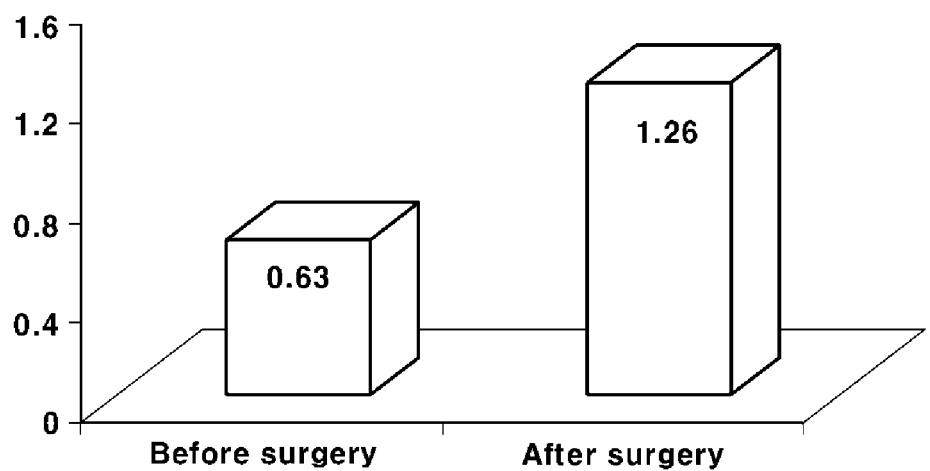
FIG. 2b

METHOD OF EVALUATING ADRENAL STEROIDS IN SALIVA COLLECTED BY COTTON SWAB

CROSS-REFERENCE TO RELATED APPLICATION

This application claims, under 35 U.S.C. § 119(a), the benefit of priority to Korean Patent Application No. 10-2018-0135752 filed on Nov. 7, 2018, the entire contents of which are incorporated herein by reference.

BACKGROUND

(a) Technical Field

The present invention relates to quantitative analysis (assay) of cortisol and its precursors and metabolites from a trace amount of saliva collected from swabs, and evaluation of metabolic activities associated with various endocrine adrenal diseases through measurement of metabolic ratios therebetween.

(b) Background Art

The adrenal gland is an endocrine organ located above the kidneys, which is divided into the adrenal cortex composed of three zones (the zona glomerulosa, the zona fasciculata and the zona reticularis) and the adrenal medulla located in the innermost part of the adrenal gland. The hormones that are metabolized and secreted in the adrenal cortex include mineralocorticoids, glucocorticoids and androgens.

Corticotropin-releasing hormone (CRH) secreted from the hypothalamus of the brain regulates the functions of adrenocortical hormones by promoting the secretion of the adrenocorticotropic hormone (ACTH) in the pituitary gland. In other words, the secretion of adrenocortical hormones is regulated by the negative feedback process of the hypothalamic-pituitary-adrenal (HPA) axis. 11β-hydroxysteroid dehydrogenase (11β-HSD), among enzymes involved in the metabolism of adrenal steroids, causes interconversion between cortisol and cortisone. Of these two isozymes, 11β-HSD type 2 oxidizes cortisol to cortisone, while 11β-HSD type 1 reduces the 11-ketone group of cortisone to form cortisol reversely. Since the activation and expression of glucocorticoids are regulated by the two isoforms having different catalytic properties, the activity of 11β-HSD can be assessed by measuring the concentration of cortisol and cortisone in vivo and by analyzing the metabolic ratios.

However, the metabolic alterations, such as Cushing's syndrome, Addison's disease, congenital adrenal hyperplasia and primary aldosteronism, occur when adrenal steroids are secreted abnormally due to an error in the feedback process or genetic defects of the 11β-HSD. Therefore, the method for measuring the level of cortisol in the blood is useful in the clinical practice as a method for predicting and evaluating dysfunctions of the HPA axis or adrenal gland-related diseases.

A number of studies to analyze the salivary concentration of cortisol and cortisone have recently been reported (*Journal of Chromatography B*, 2009, 877.29: 3771-3775; *Clinica Chimica Acta*, 2015, 451: 247-251). In contrast to the blood sampling, saliva is noninvasive and has the advantages of easy sample collection, storage and transportation. Salivette® Cortisol (Sarstedt, Nümbrecht, Germany) kit, which is most commonly used method for salivary collection, is used for the detection of steroids by mass spectrometry and enzyme immunoassay [Korean Patent KR 10-122832261]. After a filter such as synthetic cotton is placed in the mouth for 3 minutes, the filter is transferred to a test tube and centrifuged to obtain the bubble-free saliva. However, this method has a discomfort such as irritation when the filter should be held in the mouth for 3 minutes and a difficulty of collecting saliva from a subject who is physically restricted, such as an emergency patient.

Taking into consideration these aspects, a variety of adrenal steroids including cortisol and its precursors and metabolites are quantitatively analyzed only with a small amount of saliva by cotton swabs, efficacies of which are verified in the medical field [*European Journal of Applied Physiology*, 2009, 107: 743-746] and which enable saliva to be quickly and easily taken directly at home, to determine related metabolic activities, based on their respective amounts as well as ratios therebetween.

PRIOR ART

Patent Document

Korea Patent No. 10-1228322

The above information disclosed in this Background section is provided only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with the prior art.

The present inventors extracted adrenal steroids (FIG. 1) containing cortisol and cortisone from a trace amount of saliva collected using a cotton swab, and then purified and concentrated these compounds through solid-phase extraction. Furthermore, the present inventors re-dissolved the resulting extracts in an organic solvent, measuring the amount of each compound using a liquid chromatograph-mass spectrometer and evaluating the metabolic ratio, thereby completing the present invention.

It is an object of the present invention to develop an analytical method for measuring the concentration of cortisol, cortisone, and other adrenal steroids with metabolic correlations in a trace amount of saliva soaked in a swab and to evaluate the metabolic activity of adrenal hormones associated with stress response, distinguished from those of healthy people by determining the metabolic ratio.

The objects of the present invention are not limited to those described above. The objects of the present invention will be clearly understood from the following description and could be implemented by means defined in the claims and a combination thereof.

In one aspect, the present invention provides a method for quantitatively analyzing (assaying) adrenal steroids in saliva, including (a) collecting saliva using a saliva adsorption material, (b) enzymatic hydrolysis the saliva, (c) extracting the hydrolyzed salivay adrenal steroids by elution through a solid-phase extraction method using $C_1$ to $C_5$ alcohol, and (d) re-dissolving the extracted sample in an organic solvent and analyzing the resulting sample by liquid chromatography-mass spectrometry.

The saliva adsorption material may be a cotton swab.

The $C_1$ to $C_5$ alcohol solvent is a selected from methanol solvent, ethanol solvent, propanol solvent, butanol solvent and pentanol solvent.

The step of collecting saliva comprises allowing the cotton swab to retain in the mouth for about 3 to about 5 seconds.

The method may further include mixing the cotton swab soaking the saliva in step (a) with an internal standard substance of adrenal steroid to be analyzed before hydrolysis.

The enzymatic hydrolysis of step (b) may be carried out using β-glucuronidase.

The ionization method of analysis by liquid chromatography-mass spectrometry in step (d) may be electrospray ionization (ESI).

A flow rate of nitrogen spray gas used for the electrospray ionization may be from 2.0 L/min to 3.0 L/min, a vaporization temperature may be from 250 to 350° C. and a capillary voltage may be from 3.0 kV to 5.0 kV.

A column of the liquid chromatography of step (d) may have a length of 40 to 60 mm, an inner diameter of 1 to 3 mm and a filler particle size of 1.0 m to 3.0 m.

A mobile phase of the liquid chromatography of step (d) may have a concentration gradient of an aqueous solution (A) containing 5% acetonitrile and 0.1 formic acid, and a 95% acetonitrile aqueous solution (B) containing 0.1% formic acid, and a flow rate may be maintained at 0.20 mL/min to 0.30 mL/min.

A concentration gradient condition of liquid chromatography of step (d) may be set such that, from A:B=90:10 (v/v), B is adjusted to 25% at 5 minutes, B is adjusted to 60% at 8 minutes, B is adjusted to 100% at 14 minutes, B is returned to 10% of the initial composition at 18 minutes, and B is maintained at 10% for 10 minutes.

The reference materials of internal standard may include deuterium-substituted progesterone (progesterone-2,2,4,6,6,17a,21,21,21-$d_9$) for progesterone, and deuterium-substituted cortisol (cortisol-9,11,12,12-$d_4$) for cortisol, cortisone, and metabolites of cortisol.

Other aspects and preferred embodiments of the invention are discussed infra.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein:

FIG. 2 is a graph showing a metabolic ratio (F/E) of cortisol (F) to cortisone (E) in saliva collected from a swab according to the present invention, more particularly, FIG. 2a is a graph showing a difference in the metabolic ratio between patients with Cushing's disease and healthy subjects and FIG. 2b is a graph showing a variation in the metabolic ratio before and after surgery with regard to the Cushing's disease patient.

DETAILED DESCRIPTION

Figure 1:
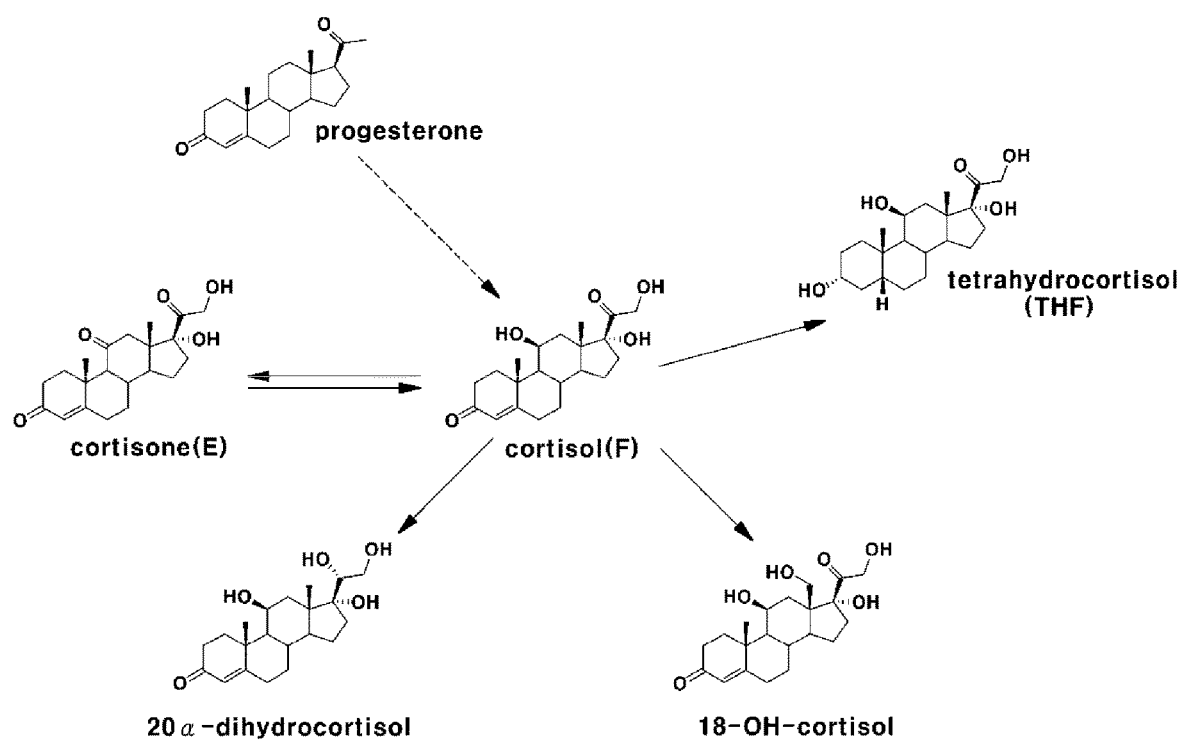
FIG. 1 shows metabolic correlations between adrenal steroids by a variety of enzymes including metabolic actions by 11β-HSDs of cortisol and cortisone to be analyzed from a trace amount of saliva collected with a cotton swab according to the present invention.

Unless context clearly indicates otherwise, all numbers, figures and/or expressions that represent ingredients, reaction conditions, polymer compositions and amounts of mixtures used in the specification are approximations that reflect various uncertainties of measurement occurring inherently in obtaining these figures among other things. For this reason, it should be understood that, in all cases, the term "about" modifies all the numbers, figures and/or expressions. In addition, when numerical ranges are disclosed in the description, these numerical ranges are continuous and include all numbers from the minimum to the maximum including the maximum within the ranges unless otherwise defined. Furthermore, when the range is referred to as an integer, it includes all integers from the minimum to the maximum including the maximum within the range, unless otherwise defined.

It should be understood that, in the specification, when the range is referred to regarding a parameter, the parameter encompasses all figures including end points disclosed within the range. For example, the range of "5 to 10" includes figures of 5, 6, 7, 8, 9, and 10, as well as arbitrary sub-ranges such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include figures such as 10%, 11%, 12% and 13%, as well as 30%, and any sub-ranges of 10% to 15%, 12% to 18%, or 20% to 30%, as well as any figures, such as 10.5%, 15.5% and 25.5%, between appropriate integers that fall within the range.

Hereinafter, the present invention will be described in detail.

The present invention includes collecting a trace amount of saliva using a cotton swab, hydrolyzing and extracting salivary adrenal steroids including cortisol and cortisone with an enzyme and then removing analytical interfering substances through solid-phase extraction and at the same time, purifying and concentrating the compounds to be analyzed. The present invention includes measuring the absolute amount of adrenal steroids by chromatographic separation combined with mass spectrometric detection and evaluating the metabolic ratio therebetween.

The present invention includes extracting the saliva using a cotton swab, extracting adrenal steroids including cortisol and cortisone from the saliva soaked in the cotton swab, purifying and concentrating the resulting extract through a solid-phase extraction method, re-dissolving the resulting product in an organic solvent, determining the concentration of the compounds by liquid chromatography-mass spectrometry, and determining the metabolic ratio between cortisol and cortisone.

Various aspects of the present invention are described below.

In one aspect of the present invention, there is provided a method for quantitatively analyzing (assaying) adrenocortical hormones in saliva, including (a) collecting saliva using a saliva adsorption material (cotton swab), (b) enzymatic hydrolysis of the salivary adrenal steroids, (c) extracting the hydrolyzed saliva by elution through a solid-phase extraction method using a $C_1$ to $C_5$ alcohol solvent (methanol solvent), and (d) re-dissolving the extracted sample in an organic solvent and analyzing the resulting sample by liquid chromatography-mass spectrometry.

The term "salivary adrenal steroids" means at least one selected from six types of hormones illustrated in FIG. 1. Therefore, the method of assaying the adrenal steroids in saliva according to the present invention can be used for simultaneous assay of all or some (two to five) of the six types of hormones and, in some cases, for assay of only one type of steroid thereamong.

In one embodiment, the saliva sample of step (a) may be obtained from any subject such as a healthy subject (hereinafter, the same will apply), a subject having a disease, or a subject in need of diagnosis of disease contraction.

In one aspect of the present invention, the step of collecting saliva includes allowing the cotton swab to retain in the mouth for 1 minute or less, preferably 3 to 5 seconds.

In one aspect of the present invention, the method includes mixing the cotton swab soaking the saliva in step (a) with an internal standard substance of the adrenal steroid to be analyzed before hydrolysis.

In one aspect of the present invention, the enzymatic hydrolysis of step (b) is carried out using β-glucuronidase.

In one aspect of the present invention, the ionization method of analysis by liquid chromatography-mass spectrometry in step (d) is electrospray ionization (ESI).

In one aspect of the present invention, the flow rate of the nitrogen spray gas used for the electrospray ionization is from 2.0 L/min to 3.0 L/min, the vaporization temperature is from 250 to 350° C., and the capillary voltage is from 3.0 kV to 5.0 kV.

In one aspect of the present invention, the column of the liquid chromatography of step (d) has a length of 40 to 60 mm, an inner diameter of 1 to 3 mm and a filler particle size of 1.0 m to 3.0 m.

In one aspect of the present invention, the mobile phase of the liquid chromatography of step (d) has a concentration gradient of an aqueous solution (A) containing 5% acetonitrile and 0.1% formic acid, and a 95% acetonitrile aqueous solution (B) containing 0.1% formic acid, and the flow rate is maintained at 0.20 ml/min to 0.30 ml/min.

In one aspect of the present invention, the concentration gradient condition of liquid chromatography of step (d) is set such that, from A:B=90:10 (v/v), B is adjusted to 25% at 5 minutes, B is adjusted to 60% at 8 minutes, B is adjusted to 100% at 14 minutes, B is returned to 10% of the initial composition at 18 minutes, and B is maintained at 10% for 10 minutes.

In one aspect of the present invention, the internal standards include deuterium-substituted progesterone (progesterone-2,2,4,6,6,17a,21,21,21-$d_9$) for progesterone, and deuterium-substituted cortisol (cortisol-9,11,12,12-$d_4$) for cortisol, cortisone and metabolites of cortisol.

Hereinafter, the present invention will be described in more detail with reference to specific examples. These examples are provided only for illustration to aid in understanding of the present invention and should not be construed as limiting the scope of the present invention.

Example 1

1) Saliva Collection

A cotton swab generally used for household and medical use was put in the saliva around the tongue of the mouth, or soaked therein for about 3-5 seconds, and then stored in a 1.5 mL microtube or a test tube with a stopper in the freezer until the experiment. For the experiment, the swab in the tube was transferred to the test tube and 20 μL of a deuterium-substituted internal standard mixture solution ($d_4$-cortisol, $d_9$-progesterone) was added thereto.

2) Enzymatic Hydrolysis 1.5 mL of phosphate buffer (pH 7.2) was added to the test tube, shaken for 5 seconds, 50 μl of β-glucuronidase was added thereto and reacted at 55° C. for 1 hour. The reaction solution was allowed to cool at room temperature.

3) Solid-Phase Extraction Method

An Oasis HLB cartridge (60 mg/3 cc, Waters, Milford, Mass., USA) was used for solid phase extraction. 2 mL of methanol and water were each allowed to flow into the cartridge twice and a swab was injected into the cartridge with a pair of tweezers. The analytes, adrenocortical hormones containing cortisol and cortisone were allowed to remain in the stationary phase by flowing the extract of 2) above. The resulting steroids were washed with a total of twice with 0.7 mL of 10% methanol in order to remove the matrix components in the saliva remaining in the stationary phase. Finally, 1 mL of methanol was allowed to flow a total of twice to obtain an eluent of the analyte in a clean test tube. Thereafter, the solvent contained in the eluent was removed at 40° C. using a nitrogen evaporator.

4) Liquid Chromatography-Mass Spectrometry

50 μL of methanol was added to the dried residue of step 3), mixed for 30 seconds and filtered at 14,000 rpm in an Ultrafree®-MC VV centrifugal filter (0.1 μm filter unit; Millipore, Bedford, Mass., USA) for 5 minutes. Then, 50 μL of 10% DMSO was added to the test tube, mixed for 30 seconds and then filtered through the same filter as above at 14,000 rpm for 5 minutes. The filtered sample was injected into a liquid chromatography vial and analyzed for an injection amount of 5 μL.

The liquid chromatograph-mass spectrometer used in the analysis is a Nexera ultrahigh performance liquid chromatography system with a LCMS-8050 triple quadrupole mass spectrometer produced by Shimadzu. The ionization method of the mass spectrometer was electrospray ionization (ESI) and uses multiple-reaction monitoring (MRM). In addition, the column used for the analysis was a Hypersil GOLD C18 produced by Thermo Fisher. The column had a length of 50 mm, an inner diameter of 2 mm and a filler particle size of 1.9 μm. The mobile phases used herein included an aqueous solution (A) containing 5% acetonitrile and 0.1% formic acid and 95% acetonitrile (B) containing 0.1% formic acid. At this time, the flow rate was 0.25 mL/min. The conditions of the gradient elution method were as follows: initially setting B to 10%, setting B to 25% at 5 minutes, setting B to 30% at 8 minutes, setting B to 60% at 10 minutes, setting B to 100% at 14 minutes, setting B to 10% of the initial composition at 18 minutes, and maintaining B at 10% for 10 minutes. The flow rate of the nitrogen spray gas used for the electrospray ionization method was 2.5 L/min, the gasification temperature was 300° C. and the capillary voltage was 4.0 kV.

Adrenal steroids including cortisol and cortisone were assayed on the basis of their respective internal standards and were qualitatively identified by comparing the height ratio of two characteristic ion peaks per compound and the retention time in the column.

5) Evaluation of Concentration of Analyte Compounds

In order to evaluate the amounts of adrenal steroids including cortisol and cortisone in the saliva collected from the swab, a standard solution of each compound was taken at each concentration and a sample for the quantitative curve was prepared. Then, a calibration curve was made, based on the ratio of the peak height of each compound to the peak height of the internal standard, obtained by treatment in the same manner as in an actual clinical sample in accordance with the description of 1), 2), 3), 4) above. The absolute amount of adrenocortical hormones was measured by applying the ratio of the compound detected from the sample to the equation of "y=ax+b" obtained based on the prepared calibration curve.

In addition, the amount of saliva collected in the swab used in the experiment could not be accurately calculated, and as the size of the swab increases, the amount of collected saliva increases. For this reason, the metabolic ratio between the compounds can be calculated based on the absolute amount of the measured compounds. The metabolic ratio (F/E) of cortisol (F) to cortisone (E) was determined to evaluate the activity of 11β-HSD.

Test Example 1

The absolute amount of cortisol and cortisone was measured using saliva soaked in swabs collected from six pituitary Cushing's disease patients and ten healthy subjects through the analytical method of Example 1 and then was compared with the case of 0.2 mL of saliva samples obtained from the same subjects using a kit (Salivette® Cortisol; Sarstedt, Nümbrecht, Germany), which had been conventionally mainly used in the clinical practice. In particular, the metabolic ratios therebetween were measured to evaluate the activity of 11β-HSD. Results are shown in Table 1.

The amounts of assayed cortisol and cortisone of the Cushing's disease patient group were 10 times and 3 times higher than those of the healthy group, respectively, and the corresponding results were similar in both conventional kit-using and swab-using methods.

TABLE 1

| Analyte | Healthy subjects | | Patients with Cushing's disease | |
|---|---|---|---|---|
| | Conventional saliva kit (ng/mL) | Swab (pg) | Conventional saliva kit (ng/mL) | Swab (pg) |
| Cortisol (F) | 3.87 ± 1.62 | 584 ± 125 | 31.11 ± 16.14 | 5378 ± 1208 |
| Cortisone (E) | 12.32 ± 4.93 | 1029 ± 367 | 31.83 ± 16.66 | 3247 ± 644 |
| F/E | 0.36 ± 0.18 | 1.93 ± 4.09 | 0.51 ± 0.74 | 0.66 ± 1.08 |

Test Example 2

The absolute amounts of adrenal steroid including cortisol and cortisone in saliva collected from swabs could be evaluated. The salivary concentrations obtained from seven Cushing's disease patients before and after surgery are shown in Table 2. It can be seen that, after surgery, all cortisol metabolites including cortisol, excluding progesterone, precursors of cortisol, decreased, and the metabolic ratio (F/E) of cortisol to cortisone, indicating the activity of 11β-HSD, increased.

TABLE 2

| Analyte | Before surgery (pg) | Immediately after surgery (pg) |
|---|---|---|
| Progesterone | 637 ± 118 | 848 ± 484 |
| 20a-hydroxycortisol | 842 ± 172 | 160 ± 39 |
| 18-hydroxycortisol | 114 ± 46 | 55 ± 10 |
| Tetrahydrocortisol | 4378 ± 442 | 1911 ± 413 |
| 21-deoxycortisol | 191 ± 113 | 178 ± 22 |
| Cortisol (F) | 4724 ± 1116 | 1529 ± 288 |
| Cortisone (E) | 3038 ± 337 | 929 ± 277 |
| F/E | 0.63 ± 0.99 | 1.26 ± 1.24 |

The present invention provides a method for evaluating adrenal grand function-related metabolic activity by determining metabolic ratios of compounds based on quantitative results of adrenal steroids including cortisol and cortisone measured from a trace amount of saliva collected with cotton swabs. In addition, the use of swabs has the advantages of obtaining samples from normal subjects as well as severe patients through non-invasive and easy sampling, and obtaining constant results, regardless of the amount of sample collected, by measuring the metabolic ratios between the compounds measured from the same sample.

The effects of the present invention are not limited to the effects mentioned above. It should be understood that the effects of the present invention include all reasonably possible effects in the following description.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for quantitatively analyzing (assaying) adrenal steroids in saliva, comprising:
   (a) collecting saliva using a saliva adsorption material;
   (b) enzymatic hydrolysis of the saliva;
   (c) extracting the hydrolyzed saliva by elution through a solid-phase extraction method using a $C_1$ to $C_5$ alcohol solvent; and
   (d) re-dissolving the extracted sample in an organic solvent and analyzing the resulting sample by liquid chromatography-mass spectrometry,
   wherein the ionization method of analysis by liquid chromatography-mass spectrometry in step (d) is electrospray ionization (ESI),
   wherein a flow rate of nitrogen spray gas used for electrospray ionization is from 2.0 L/min to 3.0 L/min, a vaporization temperature is from 250 to 350° C. and a capillary voltage is from 3.0 kV to 5.0 kV.

2. The method according to claim 1, wherein the saliva adsorption material is a cotton swab.

3. The method according to claim 1, wherein the $C_1$ to $C_5$ alcohol solvent is a selected from methanol solvent, ethanol solvent, propanol solvent, butanol solvent and pentanol solvent.

4. The method according to claim 1, wherein the step of collecting saliva comprises allowing the saliva adsorption material to retain in the mouth for 1 minute or less.

5. The method according to claim 4, further comprising mixing the saliva adsorption material soaking the saliva in step (a) with internal standards of adrenal steroid to be analyzed before hydrolysis.

6. The method according to claim 1, wherein the enzymatic hydrolysis of step (b) is carried out using β-glucuronidase.

7. The method according to claim 1, wherein a column of the liquid chromatography of step (d) has a length of 40 to 60 mm, an inner diameter of 1 to 3 mm and a filler particle size of 1.0 μm to 3.0 μm.

8. The method according to claim 1, wherein a mobile phase of the liquid chromatography of step (d) has a concentration gradient of an aqueous solution (A) containing 5% acetonitrile and 0.1% formic acid, and a 95% acetonitrile aqueous solution (B) containing 0.1% formic acid, and a flow rate is maintained at 0.20 mL/min to 0.30 mL/min.

9. The method according to claim 8, wherein a concentration gradient condition of liquid chromatography of step (d) is set such that, from A:B=90:10 (v/v), B is adjusted to 25% at 5 minutes, B is adjusted to 60% at 8 minutes, B is adjusted to 100% at 14 minutes, B is returned to 10% of the initial composition at 18 minutes, and B is maintained at 10% for 10 minutes.

10. The method according to claim 5, wherein the internal standards comprise deuterium-substituted progesterone for progesterone, and deuterium-substituted cortisol for cortisol, cortisone, and precursors and metabolites of cortisol.

\* \* \* \* \*